United States Patent
Pearcy

[11] Patent Number: 5,686,664
[45] Date of Patent: Nov. 11, 1997

[54] ATMOSPHERIC TIDE AND AIR DENSITY DETECTOR

[76] Inventor: Lee R. Pearcy, 15706 Lomita Springs Dr., San Antonio, Tex. 78247

[21] Appl. No.: 670,590

[22] Filed: Jun. 26, 1996

[51] Int. Cl.[6] ........................................... G01L 7/20
[52] U.S. Cl. ........................................... 73/384
[58] Field of Search ........................ 73/384, 386, 387, 73/370.01

[56] References Cited

U.S. PATENT DOCUMENTS

| | | |
|---|---|---|
| 2,388,542 | 11/1945 | Hobbs . |
| 2,617,304 | 11/1952 | Conover . |
| 4,263,804 | 4/1981 | Seemann ........................ 73/384 |
| 4,319,487 | 3/1982 | Haase et al. ........................ 73/384 |
| 5,040,414 | 8/1991 | Graebner ........................ 73/151 |
| 5,159,833 | 11/1992 | Graebner ........................ 73/155 |
| 5,402,116 | 3/1995 | Ashley . |

FOREIGN PATENT DOCUMENTS

| | | |
|---|---|---|
| 1589086 | 8/1990 | U.S.S.R. . |
| 454931 | 10/1936 | United Kingdom . |

Primary Examiner—Hezron E. Williams
Assistant Examiner—Jay L. Politzer

[57] ABSTRACT

An atmospheric tide and air density detector. The detector includes a chamber having an inlet and an outlet. A barometer is positioned within the chamber. An impeller, driven by a motor, is positioned in the outlet for drawing air from the chamber. An air flow restrictor is positioned in the inlet. A gauge is connected to the air flow restrictor for measuring the pressure exerted on the air flow restrictor by air drawn into the chamber during operation of the impeller.

15 Claims, 1 Drawing Sheet

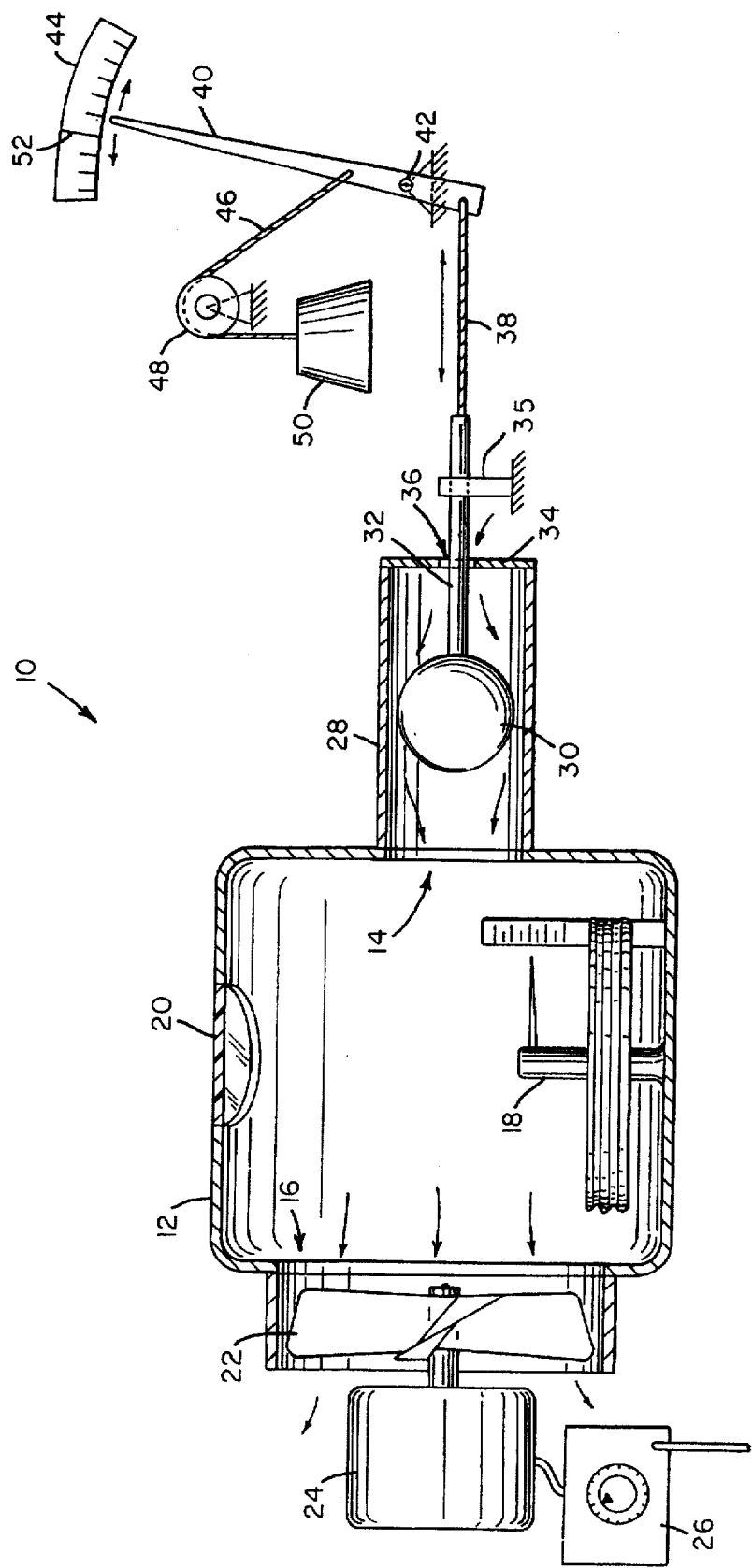

ATMOSPHERIC TIDE AND AIR DENSITY DETECTOR

FIELD OF THE INVENTION

The present invention relates generally to measuring and testing instruments and, in particular, to an apparatus for detecting atmospheric tides and variations in air density.

BACKGROUND OF THE INVENTION

Height measurements in aviation are expressed in altitudes. The five most common types are: true, absolute, indicated, pressure and density. These heights are measured in terms of distance either above ground level (AGL) or above mean sea level (MSL) which is the average height of the surface of the sea for all tidal stages.

True altitude is the exact distance above mean sea level. The heights of all fixed, non-changeable objects are given in true altitude. This includes field elevations and obstructions such as mountains, radio antennas and towers. These measurements do not change with varying atmospheric conditions.

Absolute altitude is the height of an aircraft above the surface or terrain over which it is flying. This altitude is typically abbreviated as feet AGL.

Indicated altitude is displayed on the aircraft altimeter in feet above mean sea level when the altimeter is adjusted to the current barometric setting. If the aircraft is on the ground and the altimeter is set to the local altimeter setting, for instance, is will read field elevation, or true altitude of the field, assuming no instrument error.

Pressure altitude is equivalent to an elevation measured above a standard pressure level. In an aircraft, it is obtained by setting 29.92 in the barometric pressure window, then reading the pressure altitude from the altimeter. This altitude is used to obtain computer solutions for such items as true airspeed, density altitude and true altitude.

Density altitude is pressure altitude corrected for non-standard temperature variations. It is an important altitude since it is directly related to an aircraft's performance in terms of engine power, thrust and lift. Thus, many aircraft performance charts, used to plan most aircraft flights, are based on this value.

Tide generating forces arise from the gravitational action of the Sun and the Moon. The tidal forces act to generate stresses in all parts of the Earth and give rise to relative movements of the matter of the solid Earth, ocean and atmosphere. So-called atmospheric tides can modify observed pressure and density altitudes. Thus, detecting atmospheric tides can be important in planning the flight of an aircraft and predicting changes in the weather.

SUMMARY OF THE INVENTION

Accordingly, it is a principal object of the invention to provide a device capable of detecting atmospheric tides.

It is an object of the invention to provide a device which is compact in size, lightweight, inexpensive, dependable and fully effective in detecting atmospheric tides and variations in air density.

Briefly, the atmospheric tide and air density detector in accordance with this invention achieves the intended objects by featuring a vacuum chamber having an air inlet and an air outlet. An aneroid barometer is positioned within the chamber and may be viewed through a window in the chamber. An impeller, driven by a motor, is positioned in the outlet for drawing air from the chamber. An air flow restrictor is positioned in the inlet. A gauge is connected to the air flow restrictor for measuring the pressure exerted on the air flow restrictor by air drawn into the chamber during operation of the impeller. Pressure readings obtained from the aneroid barometer over time may be compared to aid in detecting atmospheric tides.

The foregoing and other objects, features and advantages of the present invention will become readily apparent upon further review of the following detailed description of the preferred embodiment as illustrated in the accompanying drawing.

BRIEF DESCRIPTION OF THE DRAWING

The present invention may be more readily described with reference to the accompanying drawing figure which is a side elevational view of an atmospheric tide and air density detector having portions broken away to reveal interior details thereof.

DETAILED DESCRIPTION OF THE PREFERRED EMBODIMENT

Referring now to the FIG., an atmospheric tide and air density detector in accordance with the present invention is shown at 10. As illustrated, the detector 10 includes a vacuum chamber 12 having inlet and outlet openings 14 and 16, respectively, at its opposite ends. Positioned within the vacuum chamber 12 is an aneroid barometer 18 of conventional construction. So that the barometer 18 can be viewed by users of the detector 10, a transparent window 20 is provided in the top of the chamber 12.

Positioned adjacent the outlet opening 16 is an impeller 22 for drawing air from the chamber 12 and discharging it to the atmosphere. The impeller 22 is connected to an electric motor 24 which may be selectively energized to rotate the impeller. The motor 24 is provided with a speed control device, such as a rheostat 26, so that its rotational speed, and consequently that of the impeller 22, can be infinitely varied within operational limits.

One end of a cylindrical conduit 28 is connected to the inlet opening 14 of the chamber 12. Loosely fitted within the conduit 28 is a spherical air impact target 30 formed of plastic or other lightweight material. (In the preferred embodiment, the conduit 28 has an inner diameter of 1.25 inches whereas the target 30 has a 1 inch diameter.) A rigid shaft 32 extends longitudinally from the target 30 and to the exterior of the conduit 28 where it is supported by a guide 35. A ring-shaped plate 34 is secured to the free end of the conduit 28. A circular orifice 36 in the center of the plate 34 permits passage of the shaft 32.

The free end of the shaft 32 is connected by means of a short cable 38 to the bottom of a pointer 40 arranged to pivot on a pin 42. The top of the pointer 40 is positioned adjacent a fixed scale 44 which may be ruled in any suitable manner. Thus, by noting the position of the top of the pointer 40 opposite the scale 44, a user of the detector 10 may conveniently measure the position of the target 30 within the conduit 28 at any time.

A second cable 46 is secured to the pointer 40 at a location between its top and the pivot pin 42. As shown, the cable 46 extends laterally from the pointer 40 a short distance and then falls over a pulley 48. Suspended below the pulley 48 from the free end of the cable 46 is a weight 50. The force exerted by the weight 50 through the cable 46 provides a bias against the tension exerted on the pointer 40 through the first cable 38.

Adjacent the vacuum chamber 12 is usually positioned a second aneroid barometer and a thermometer (both not shown) for use in calibrating the detector 10.

To use the detector 10, an ambient air pressure reading is initially taken from the barometer 18 with the impeller 22 being motionless. Next, the electric motor 24 is energized and its speed is controlled by the rheostat 26 to decrease the barometric pressure within the vacuum chamber 12. While maintaining a constant pressure drawdown within the vacuum chamber 12, a second pressure reading is taken from the barometer 18 with the top of the pointer 40 maintained adjacent an arbitrary reference point such as point 52 on the scale 44.

By subtracting the second barometric reading from the first, a recorded pressure drawdown value is obtained. The recorded pressure drawdown value can then be compared with an expected pressure drawdown value to aid in tracking the motion of an atmospheric wave.

The expected pressure drawdown value is determined by first obtaining the average recorded pressure drawdown values over a period of time, say, two weeks. This average drawdown value is then corrected for temperature and pressure, whose values are obtained from the thermostat and barometer mentioned above which are kept remote from the vacuum chamber 12, at the time any recorded drawdown pressure is obtained. The temperature and pressure correction yields an expected pressure drawdown value, i.e., the value that should have been obtained during the subtraction step noted in the previous paragraph absent the presence of an atmospheric wave.

The difference between the recorded and expected pressure drawdown values at any given time is important and may be compared with similar differences at other times to track the motion of a passing atmospheric wave. Generally, however, when the expected pressure drawdown value is greater than the recorded value, the air in the atmosphere above the detector 10 is more dense than anticipated and is little affected by the gravitational pull exerted by the Sun or Moon. This condition may be considered to be the trough between adjacent atmospheric waves. On the other hand, should the expected pressure drawdown value be lower than the recorded value at any given point in time, the air in the atmosphere above the detector 10 is less dense than anticipated and is being affected by the pull of the Sun or Moon. The detector 10, then, is in the presence of the crest of a gravitational wave.

Although the construction and use of one detector 10 is described hereinabove, it should be understood that typical atmospheric waves are believed to be large structures encompassing perhaps hundreds of square miles. Thus, fully measuring and assessing the motion of an atmospheric wave would require a group of detectors 10. The benefits to be derived from this detector group would, however, improve weather forecasting capabilities.

While the detector 10 has been described with a high degree of particularity, it will be appreciated by those skilled in the art that numerous modifications and substitutions may be made thereto. For example, pressure gages having either liquid columns, electrical pressure transducers or other expansible metallic elements may be substituted for the aneroid barometer 18. Furthermore, a flat plate or other obstruction to flow may be substituted for the target 30 held by the shaft 32 within the conduit 28. Therefore, it is to be understood that the present invention is not limited to the sole embodiment described above, but encompasses any and all embodiments within the scope of the following claims.

I claim:

1. An atmospheric tide and air density detector, comprising:
    a chamber having an inlet and an outlet;
    a barometer in said chamber;
    an impeller in said outlet for drawing air from said chamber;
    a motor for driving said impeller;
    an air flow restrictor positioned in said inlet; and,
    a gauge connected to said air flow restrictor for measuring the pressure exerted on said air flow restrictor by air drawn into said chamber during operation of said impeller.

2. The atmospheric tide and air density detector according to claim 1 wherein said chamber has a window for visually inspecting said barometer.

3. The atmospheric tide and air density detector according to claim 1 wherein said barometer includes a sealed bellows for sensing variations in air pressure.

4. The atmospheric tide and air density detector according to claim 1 wherein said motor is electrically powered.

5. The atmospheric tide and air density detector according to claim 4 further comprising a rheostat connected to said motor for controlling the speed thereof.

6. The atmospheric tide and air density detector according to claim 1 wherein said air flow restrictor is centrally positioned within said inlet so as to permit air to flow around said air flow restrictor.

7. The atmospheric tide and air density detector according to claim 1 wherein said air flow restrictor is a ball.

8. The atmospheric tide and air density detector according to claim 1 wherein said gauge includes a pointer in communication with said air flow restrictor.

9. The atmospheric tide and air density detector according to claim 1 wherein said gauge includes:
    a pointer having opposed indicating and attaching ends, said attaching end being connected to said air flow restrictor;
    a ruled scale fixedly positioned adjacent said indicating end of said pointer;
    a pivot pin secured to said pointer between said indicating and attaching ends for pivotally supporting said pointer; and,
    means for biasing said pointer connected to said indicating end of said pointer.

10. An atmospheric tide and air density detector, comprising:
    a chamber having an inlet open to the atmosphere and an outlet open to the atmosphere;
    means for detecting changes in air pressure within said chamber;
    means for drawing air from said chamber;
    means for restricting the flow of air through said inlet; and,
    means, in communication with said restricting means, for detecting changes in air pressure within said inlet.

11. The atmospheric tide and air density detector according to claim 10 wherein said means for detecting changes in air pressure within said chamber comprise a barometer.

12. The atmospheric tide and air density detector according to claim 10 wherein said means for drawing air from said chamber comprise an impeller.

13. The atmospheric tide and air density detector according to claim 10 wherein said means for restricting the flow of air through said inlet comprise an air flow restrictor centrally positioned within said inlet so as to permit air to flow around said air flow restrictor.

14. The atmospheric tide and air density detector according to claim 13 wherein said means for detecting changes in air pressure within said inlet comprise:

a pointer having opposed indicating and attaching ends, said attaching end being connected to said air flow restrictor;

a ruled scale fixedly positioned adjacent said indicating end of said pointer;

a pivot pin secured to said pointer between said indicating and attaching ends for pivotally supporting said pointer; and, biasing means connected to said indicating end of said pointer.

15. An air density detector, comprising:

a chamber having an air inlet open to the atmosphere and an air outlet open to the atmosphere;

an aneroid barometer in said chamber;

a window in said chamber for visually inspecting said barometer;

an impeller in said outlet for drawing air from said chamber;

an electric motor for driving said impeller;

a rheostat connected to said motor for controlling the speed thereof;

an air flow restrictor positioned within said inlet so as to allow the flow of air around said air flow restrictor; and, a gauge connected to said air flow restrictor for measuring the pressure exerted on said air flow restrictor by air drawn into said chamber during operation of said impeller.

* * * * *